United States Patent [19]

Scola

[11] Patent Number: 4,863,640
[45] Date of Patent: Sep. 5, 1989

[54] MONOMERS FOR HIGH TEMPERATURE FLUORINATED POLYIMIDES

[75] Inventor: Daniel A. Scola, Glastonbury, Conn.

[73] Assignee: United Technologies Corporation, Hartford, Conn.

[21] Appl. No.: 867,716

[22] Filed: May 27, 1986

[51] Int. Cl.[4] .................. C07C 15/16; C09B 11/04
[52] U.S. Cl. ........................ 549/241; 560/14; 560/21; 560/57; 560/76; 560/83; 562/54; 562/435; 562/468; 562/488
[58] Field of Search .................. 260/389, 395, 386; 549/241

[56] References Cited

U.S. PATENT DOCUMENTS

| | | | |
|---|---|---|---|
| 3,310,573 | 3/1967 | Coe | 260/346.3 |
| 3,356,648 | 12/1967 | Rogers | 260/47 |
| 3,705,870 | 12/1972 | Darmory et al. | 260/30.2 R |
| 4,063,984 | 12/1977 | Critchley | 260/49.75 |
| 4,196,277 | 4/1980 | Jones et al. | 528/208 |
| 4,203,922 | 5/1980 | Jones et al. | 260/570 R |
| 4,307,024 | 12/1981 | Kray et al. | 260/389 |
| 4,336,175 | 6/1982 | Gibbs | 524/726 |
| 4,569,988 | 2/1986 | Scola et al. | 528/353 |

FOREIGN PATENT DOCUMENTS

| | | | |
|---|---|---|---|
| 620114 | 3/1949 | United Kingdom | 260/390 |
| 1062435 | 3/1967 | United Kingdom . | |
| 1216505 | 12/1970 | United Kingdom . | |

OTHER PUBLICATIONS

Paper titled "Synthesis of Multifunctional Triarylfluoreithanes, 1. Condensation of Fluoro Ketones" by William D. Kray and Rober W. Rosser; J. Org. Chem., vol. 42, No. 7, 1977, pp. 1186–1189.

Primary Examiner—Richard L. Raymond
Assistant Examiner—Raymond Covington

[57] ABSTRACT

Fluorinated aromatic hydrocarbons including fluorinated aromatic carboxylic acids fluorinated aromatic dianhydrides and fluorinated aromatic dialkyl esters that serve as precursor monomers for high temperature fluorinated polyimides. The fluorinated aromatic carboxylic acid monomer comprises:

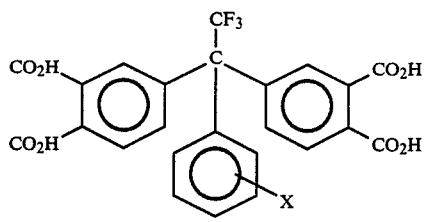

wherein X is hydrogen, carboxyl, sulfonic acid, hydroxy, alkyl, halogen or nitro and hydrates of said acids. The fluorinated aromatic dianhydride monomer comprises:

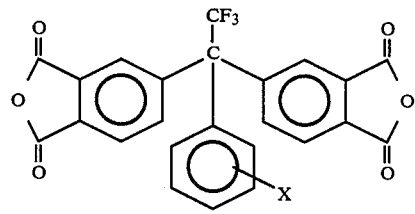

wherein x is hydrogen, carboxyl, sulfonic acid, hydroxy, alkyl, halogen or nitro. The fluorinated aromatic dialkyl ester monomer comprises:

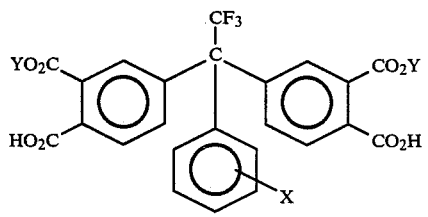

wherein X is hydrogen, carboxyl, sulfonic acid, hydroxy, alkyl, halogen or nitro and Y is an alkyl group and hydrates of said esters.

10 Claims, No Drawings

MONOMERS FOR HIGH TEMPERATURE FLUORINATED POLYIMIDES

CROSS REFERENCE

This application relates to commonly assigned co-pending applications Ser. Nos. 867,719 and 867,720 filed on even date herewith entitled "High Temperature Fluorinated Polymer" and "High Temperature Fluorinated Polyimides" respectively, which disclose material related to that contained herein the disclosures of which are hereby incorporated by reference.

TECHNICAL FIELD

The field of art to which this invention pertains is fluorinated aromatic hydrocarbons and method of making the same.

BACKGROUND ART

Composites are increasingly used as replacements for metal components in aerospace applications. Composites offer a variety of advantages over their metal counterparts such as lightweightness, improved strength, and the use of fewer components. Many of these components must be capable of withstanding elevated temperatures of about 200 degrees centigrade (°C.) to about 400° C. (e.g. when they are in close proximity to gas turbine engines). A few high temperature polymers exist, such as PMR-15 TM polyimide NASA Lewis which is licensed to various companies (Ferro Corporation, U.S. Polymeric, etc.; Culver City, Calif. and Santa Ana, Calif.), HR600 TM polyimide (National Starch, Bridgewater, N.J.) and NR150B2 TM polyimide (E. I. DuPont de Nemours, Wilmington, Del.). However, high temperatures of about 300° C. to about 400° C. and high pressures of about 1000 psi to about 5000 psi can be required to process these resins into composites or resin parts. At these high temperatures, the pressure bags that are used in composite autoclave processing can fail.

Accordingly, there has been a constant search in this field of art for high temperature resins and their precursor monomers that can be processed at lower temperatures and pressures.

DISCLOSURE OF INVENTION

The disclosure of this invention is directed to fluorinated aromatic carboxylic acid monomer precursors for high temperature fluorinated polyimides comprising:

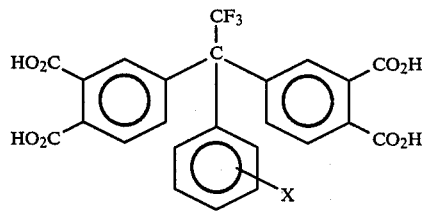

wherein X is hydrogen, carboxyl, sulfonic acid, hydroxy, alkyl, halogen or nitro and hydrates of said acids.

Another aspect of this invention is directed to fluorinated aromatic dianhydride monomer precursors for high temperature fluorinated polyimides comprising:

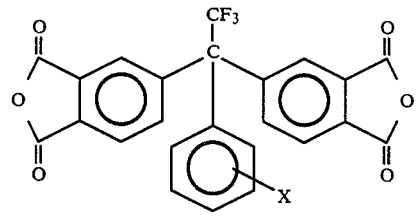

wherein x is hydrogen, carboxyl, sulfonic acid, hydroxy, alkyl, halogen or nitro.

Another aspect of this invention is directed to fluorinated fluorinated aromatic dialkyl ester monomer precursors for high temperature fluorinated polyimides comprising:

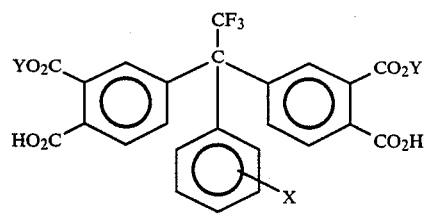

wherein X is hydrogen, carboxyl, sulfonic acid, hydroxy, alkyl, halogen or nitro and Y is an alkyl group and hydrates of said esters.

These fluorinated aromaic hydrocarbons provide the monomers for high temperature polymers that are useful in the aerospace industry. Thus they make a significant contribution to the polymer arts.

The foregoing and other objects, features and advantages will be apparent from the specification, claims which will illustrate an embodiment of the invention.

BEST MODE FOR CARRYING OUT THE INVENTION

Xylene availale from J. T. Baker Company, (Phillipsburg, N.J.) and trifluoroacetophenone available from Aldrich Chemical Company (Milwaukee, Wisc.) react in the presence of a strong Friedel-Crafts acid catalyst such as trifluoromethyl sulfonic acid available from Aldrich Chemical Company (Milwaukee, Wisc.) resulting in a monomer intermediate of these fluorinated aromatic hydrocarbons. The reaction product is 1-phenyl-1,1-bis(3,4-xylyl)-2,2,2-trifluoroethane depicted empirically below and hereinafter referred to as 3F -tetramethyl and derivatives thereof.

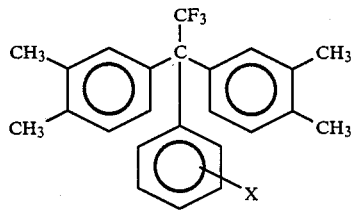

The 3F-tetramethyl derivative above has a variety of derivatives. When X is a halogen or nitro group, especially in the ortho position, the resultant polyimides described in commonly assigned copending application 867,720 have a typically lower Tg but can be processed at lower temperatures and pressures and have inherently greater fire resistance. When X is carboxyl, sulfonic acid, hydroxy or an alkyl group preferably in the para position, the resultant polyimides described in commonly assigned copending application 867,720 have greater strengths due to greater cross-linking but are processed at higher temperatures and pressures than the other above described derivatives. These 3F-tetramethyl derivatives can be made using the above reaction and the trifluoroacetophenone derivative that corresponds to the desired 3F-tetramethyl derivative. These trifluoroacetophenone derivatives are available generally from Aldrich Chemical Company (Milwaukee, Wisc.).

3F-tetramethyl or its derivatives are oxidized in the presence of a strong oxidizing agent such as potassium permanganate, chromic acid or nitric acid available from J. T. Baker Chemical Company (Phillipsburg, N.J.) to form the corresponding tetra-acid; 4,4' (2,2,2-trifluoro-1-phenylethylidene)-biphthalic tetracarboxylic acid, also called 1,1,1-trifluoro-2-phenyl-2-bis(4,4'-phthalic acid)ethane or its derivatives which are depicted empirically below and hereinafter referred to as 3F-tetra-acid and derivatives thereof, where X is hydrogen, carboxyl, sulfonic acid, hydroxy, alkyl, halogen, or nitro, including hydrates thereof.

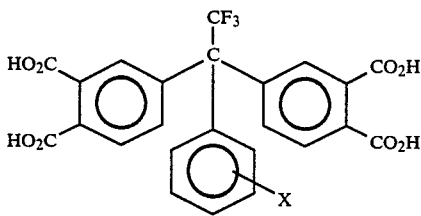

3F-tetra-acid or its derivatives are dehydrated preferably with heat or alternatively with an anhydride such as an aliphatic anhydride preferably acetic, propionic or butanoic anhydride. Acetic anhydride is available from J. T. Baker Chemical Company (Phillipsburg, N.J.). The dehydration results in the dianhydride; 4,4'(2,2,2-trifluoro-1-phenylethylidene)-biphthalic tetra carboxylic acid dianhydride or derivatives which are depicted empirically below and hereinafter referred to as 3F-dianhydride and derivatives thereof, where X is hydrogen, carboxyl, sulfonic acid, hydroxy, alkyl, halogen, or nitro.

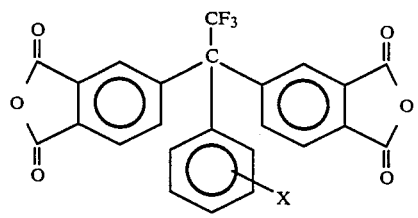

The dianhydride 4,4'(2,2,2-trifluoro-1-phenylethylidene)-biphthalic tetra carboxylic acid dianhydride described above can be esterified with an alcohol, preferably a short chain alcohol, such as ethanol available from J. T. Baker Company (Phillipsburg, N.J.) to produce the dialkylester; 4,4'(2,2,2-trifluoro-1-phenylethylidene)-bipthalic tetracarboxylic acid dialkylester, hereinafter referred to as 3F-dialkylester depicted empirically below and derivatives thereof where X is hydrogen, carboxyl, sulfonic acid, hydroxy, alkyl, halogen, or nitro and hydrates thereof. Y is preferably an alkyl group.

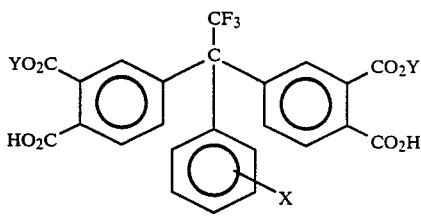

The above dialkylester can be reacted with an alcohol solution of the above described diamines to form the polyamic acid technically named poly(arylene or alkylene 4,4'-2,2,2-trifluoro-phenylethylidene bipthalamic acid) described in commonly assigned copending application 867,720.

The monomers of this disclosure may be made using the above-described compounds and the following procedures. It is preferable to dissolve trifluoroacetophenone in a molar excess preferably about 10 to 1 of xylene at about 20° C. to about 25° C. (room temperature) under slight agitation for about 2–4 days. The molar excess is preferred because it increases the product yield. In contrast to the following autoclave method or azeotropic method described in Example 2 below, this method is preferable because yields are considerably higher and it is carried out under ambient conditions. The 3F-tetramethyl compound precipitates out is easily filtered and washed with an alcohol solution yielding a clean white solid. Alternatively, the xylene and trifluoroacetophenone can be mixed in an autoclave under ambient pressures for about 3 to about 5 hours at a temperature of about 125° C. to about 175° C. in the presence of about 4 to about 12 weight percent (%) trifluoromethyl sulfonic acid yielding the 3F-tetramethyl compound. This reaction is depicted empirically below.

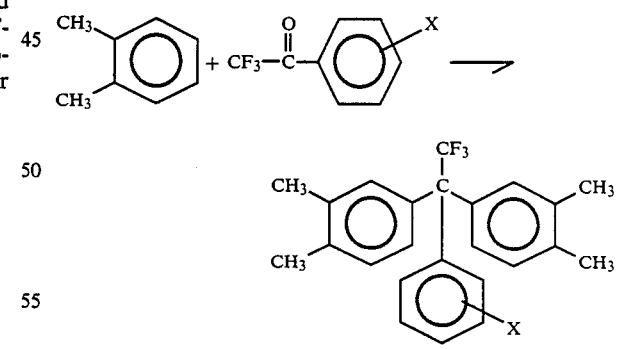

About 25% to about 35% nitric acid (about 3.0 moles nitric acid per mole of methyl group to about 3.6 moles nitric acid per methyl group) is added to the 3F tetramethyl compound and the resulting slurry is heated at about 150° C. to about 250° C. for about 0.5 to about 1.5 hours in an autoclave under ambient pressure. Beyond about 1.5 hours a high percentage of undesirable side products such as nitration products result. After heating the reaction is cooled rapidly resulting in the 3F-tetra acid. This reaction is depicted empirically below.

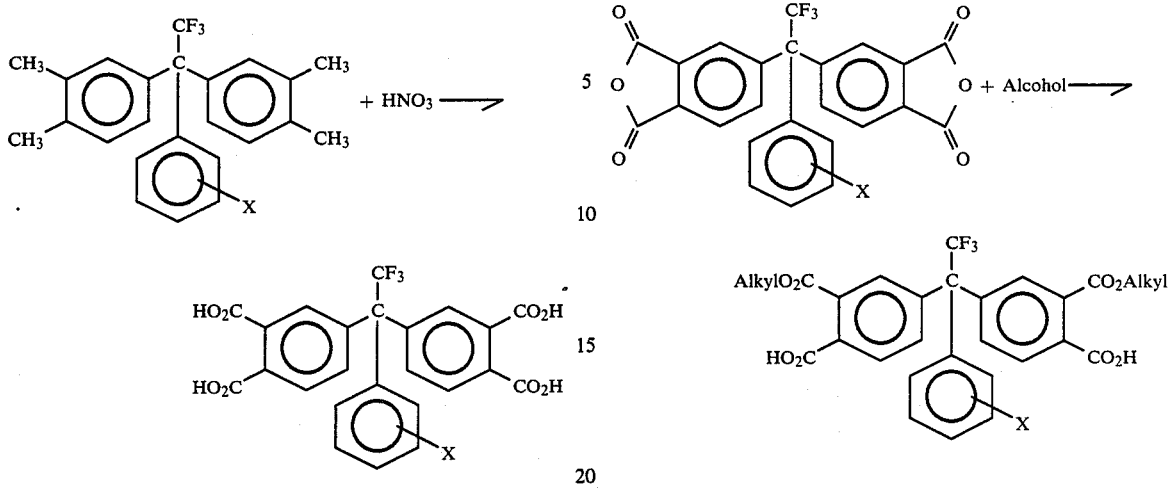

It is preferable to treat the 3F-tetra acid at about 180° C. to about 240° C. for about 1 to about 3 hours under about 1 mm to about 30 mm vacuum because this results in a high yield of pure product. Under these conditions, water is removed and the 3F-dianhydride is formed. Alternatively, the 3F-tetra acid is dissolved in about 5 to about 15 molar excess of acetic anhydride and refluxed for about 0.5 to about 2 hours. It is subsequently cooled to about 0° C. to about 25° C. (room temperature) to precipitate a white crystalline solid (3F-dianhydride) which is filtered and air-dried. This reaction is depicted empirically below.

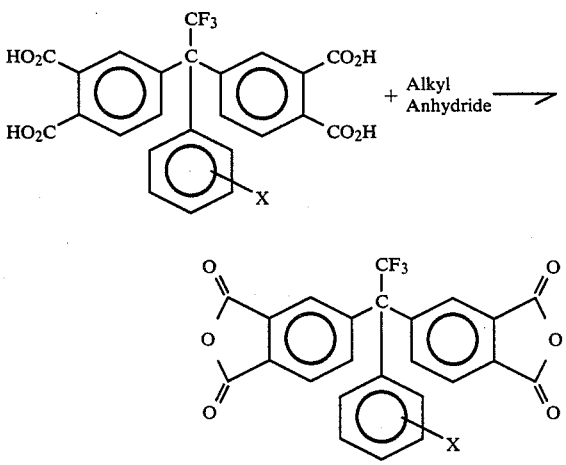

The dianhydride described above can be esterified. The 3F-dianhydride is preferably dissolved in about 5 to about 10 molar excess of alcohol and refluxed for about 2 to about 4 hours at which time the excess alcohol is evaporated under 30 mm to about 1 mm vacuum at a temperature below about 40° C. Above about 40° C., the reverse reaction to dianhydride can occur. The below reaction and resultant clear amber solid 3F-dialkylester are depicted empirically below.

EXAMPLE I

Into a three neck round bottom flask equipped with stirrer reflux condenser and addition funnel was added 600 ml o-xylene, 50 g (0.287 mole) of trifluoroacetophenone and 25 g of trifluoromethane sulfonic acid. The reaction mixture was stirred for 72 hours at room temperature. The solution was washed with water to remove trifluoromethane sulfonic acid. A white solid precipitated from the washed organic layer, which after filtration, washing in cold ethanol, and drying, weighed 81.4 g (77% yield) mp 178.5°–180° C.

This 3F-tetramethyl compound was characterized by infrared and NMR spectroscopy, high pressure liquid chromatography for purity and elemental analyses.

Calculated $C_{24}H_{23}F_3$: C, 78.23; H, 6.29; F, 15.47
Found: C, 78.12; H, 6.28; F, 15.47

In a stainless steel autoclave 10 g (0.027 mole) of 3F-tetramethyl and 6.8 ml of 30% nitric acid were added. The autoclave was sealed and the reaction mixture was heated to 200° C. for 1 hour and then cooled immediately. The cooled mixture was removed from the reaction vessel. The excess acid was removed in a rotary evaporator to yield a pale yellow solid (14.2 g). The pale solid was dried at 80° C. in a vacuum to yield a pale yellow crystalline material 13.6 g (96% yield) mp 110°–114° C. (foamed). Elemental analyses showed it to be the dihydrate of the 3F-tetra-acid.

Calculated $C_{24}H_{19}F_3O_{10}$: C, 54.98; H, 3.65; F, 10.87;
Found: C, 54.70; H, 3.46; F, 10.84

The monohydrate of the 3F-tetra-acid was obtained by treatment of the product isolated as described above at 60° C. for 1 hour.

Calculated $C_{24}H_{17}F_3O_9$: C, 56.92; H, 3.28; F, 11.26
Found: C, 56.21; H, 3.02; F, 10.38

The tetra-acid 8.20 g (0.0168 mole) was heated at 190° C. for 1 hour to yield 7.729 g dianhydride, mp 120°–125° C. Elemental analyses gave the following results:

Calculated $C_{24}H_{11}F_3O_6$: C, 63.72; H, 2.45; F, 12.60
Found: C, 62.2; H, 2.48; F, 12.51.

2.24 grams (g) (0.05 mole) 3F-dianhydride was dissolved in 12 cubic centimeters (cc) of absolute ethanol and refluxed for about 40 minutes to yield 2.70 g (0.05 mole) 3F-diethylester.

The 3F-diethylester-alcohol solution was added over a period of about 15 minutes at room temperature to a solution of p-phenylenediamine 0.54 grams (0.05 mole) in 10 cc absolute ethanol resulting in a 3F-polymeric acid solution. A portion of the solution was concentrated to a solid by heating at 40° C. to evaporate the alcohol. The resultant powder was processed into a polymer disc at 200° C., 1000 psi over a period of 1 hour. The polymer was further polymerized at 310° C. for 1 hour to obtain the polymer yielding the glass transition temperature detailed in Table II.

A second portion of the above 3F-polyamic solution was used to impregnate a Celion 6000 graphite fiber tow at room temperature. The solvent was allowed to evaporate and the tape was assembled into layers to form a laminate structur. The prepolymer impregnated graphite fiber was heated to 200° C. under 200 psi pressure to form a polyimide composite. Further consolidation and polymerization of the graphite polymer material was carried out by raising the temperature to 325° C. under 1000 psi pressure. It was held at these conditions for 1 hour yielding the composite properties detailed in Table II.

Example II

To a 3 neck flask equipped with a stirrer and Dean-Stark tube to which was attached a condenser was added 300 g of o-xylene, trifluoroacetophenone (25 g, 0.143 mole) and trifluoromethane sulfonic acid (25 ml). The solution was refluxed for 43 hours, while removing water via the Dean-Stark tube. The reaction mixture was cooled, washed with water to remove trifluoromethane sulfonic acid. The organic layer was driven over anhydrous calcium sulfate filtered, an concentrated to a volume of 200 ml. The crystalline product which precipitates out, was filtered, washed with cold ethanol and air-dried to yield 21 g of (40% yield) white solid, mp 174°–176° C. Yields by this method varied from 14 to 40%.

Example III

An autoclave was charged with 20.3 g (0.144 mole) of 2,2,2-trifluoroacetophenone 334 ml (300 g, 2.82 mole) of o-xylene and 12.5 ml of trifluoromethane sulfonic acid. The autoclave was sealed and heated to 125° C. and maintained at this temperature for four (4) hours. The autoclave mixture was cooled to room temperature, opened, and its contents were emptied into a 600 ml beaker. The autoclave was washed with o-xylene (2×50 ml). The organic reaction mixture was washed with water until a neutral water was was obtained. The o-xylene was dried over anhydrous magnesium sulfate. The solution was filtered, and then concentrated on a rotary evaporator to a volume of about 50 ml, which contained a crystalline product in a red-brown oily mixture. Ethanol (25 ml) was aded, the mixture was filtered and the solid was washed with cold ethanol (10 ml), the solid was air dried to yield a white crystalline product (31 g), 58.5% yield, mp 174°–176° C. Yields by the autoclave method varied from 17 to 71 wt %.

Example IV

To a 500 ml round bottom flask equipped with a stirrer, reflux condenser and glass stopper was added ten grams (10 g, 0.027 mole) of 3F-tetramethyl, 244 ml of pyridine and 80 ml of H$_2$O. The mixture was brought to reflux, and potassium permanganate (24.48 g, 0.155 mole) was added in portions over a period of one-half hour. The reaction mixture was refluxed for an additional two hours. The hot reaction mixture was filtered through a bed of Celite TM diatomaceous earth (Johns Manvile Products Corp.) to remove MnO$_2$ which was washed with a hot solution of pyridine/water (25 ml/33 ml). The filtrate was reduced to 1/5 its original volume, and returned to the reaction flask. It was brought to reflux temperature, after which time additional KMnO$_4$ (29.9 g, 0.189 mole) was added over a period of one-half hour. The mixture was filtered through celite to remove MnO$_2$. The filtrate was concentrated on a hot plate in a hood to remove pyridine while continually adding water until no odor of pyridine persisted. The concentrated aqueous solution was acidified with concentrated hydrochloric acid. The white crystalline solid was filtered and dried at 50° C. for four hours. It weighed 9.5 g (85.6% yield), mp 110°–114° C., foamed at 140°–160° C., and formed a glass at about 178° C. This solid was placed in a soxlet thimble and extracted with acetone to separate traces of inorganic material. The acetone extract was concentrated to a white solid (9.1 g) free of inorganic impurity.

The solid was treated at 60° C. for 4 hrs. under vacuum to yield a white solid, mp 110°–114° C. (foam). Elemental analyses gave the following results for the monohydrate.

Calculated for C$_{24}$H$_{17}$F$_3$O$_9$; C, 56.2, H, 3.02, F, 10.38 Found: C, 56.07; H, 3.89; F, 9.91

The hydrate-free tetra-acid was obtained by treating the hydrated tetra-acid at 175° C. for 16 hours in vacuum to yield the white solid, mp 159°–164° C. Elemental analyses gave the following results.

Calculated for C$_{24}$H$_{15}$F$_3$O$_8$; C, 59.02; H, 3.09; F, 11.67 Found: C, 58.92; H, 2.96; F, 11.32

The infrared and NMR spectra of all products were consistent with tetra-acid.

The above-described monomers are usful for example as precursors to the formation of high temperature polyimides such as those described in commonly assigned copending application 867,720.

Specifically, the 3F dianhydride is reacted with diamines resulting in the immediate formation of polyamic acid, technically termed poly(arylene or alkylene 4,4'-(2,2,2-trifluoro-phenylethylidene bipthalamic acid) which is depicted empirically below. The reaction is preferably carried out in an aprotic solvent and it is especially preferred that it is carried out in dimethylformamide, dimethylacetamide, diglyme, dioxane, N-methylpyrrolidine, dimethylsulfoxide because this results in higher molecular weight polymers which exhibit better properties (e.g. strength). The above process is preferred to the alternative intermediate esterification of the dianhydride described below since that process entails an extra step with no offsetting advantages.

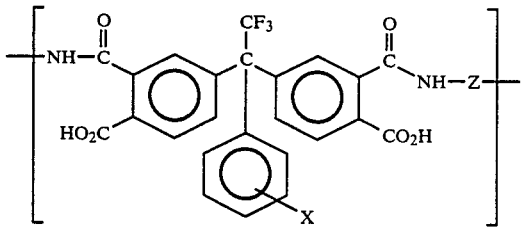

Alternatively, equal molar mounts of dialkylester and an alcohol solution or aprotic solution of diamine are mixed and the alcohol or solvent is evaporated off at room temperatures over a period of about ½ hour to about 2 hours yielding 3F-polyamic acid. This reaction is depicted empirically below.

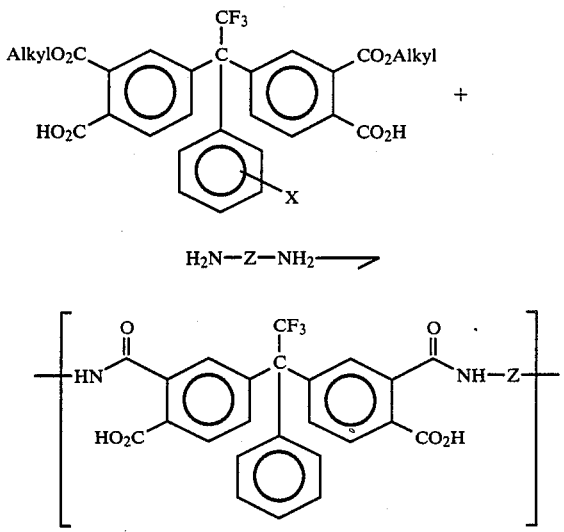

The resultant polyamic acid or solution can be processed to the polyimide by a variety of paths. It can be used to impregnate a fiber bundle to yield polyamic acid film with traces of solvent. The polyamic solution can be heated to form a polyamic acid film. For example, the polyamic acid solution or film is heated for about 1 hour to about 4 hours at temperatures of about 100° C. to about 300° C. utilizing optional pressure resulting in the polyimide. It is preferred to post-cure the polymer at temperatures of about 300° C. to about 350° C. for about 2 hours to about 24 hours under optional pressure of about 100 psi to about 2000 psi to achieve the maximum high temperature polymer properties.

Alternatively, the polyamic acid solid derived from solution by precipitation with water is processed at about 150° C. to about 300° C., preferably under pressures of about 200 to about 1000 psi. The polymer is processed (post-cured) at about 300° C. to about 350° C. for about 1 to about 24 hours to yield the polyimide of this disclosure. Alternatively, the polyamic acid solid can be added to ortho toluene or xylene and refluxed while removing water to produce the polyimide.

These polyimides can be used as composite resins in conjunction with a variety of fibers such as graphite, carbon, polymeric fibers, glass, silicon carbide Kevlar TM polyimide fiber available from E. I. DuPont de Nemours, (Wilmington, Del.). It is preferred that the fibers are graphite or boron because of the high modulus. An exemplary material is Celion TM 6000 fiber available from BASF (Parsippany, N.J.). Another is HMS TM fiber available from Hercules (Wilmington, Del.).

The polyamic acid solution can be used to impregnate tapes for composites which are then treated at elevated temperaturesof about 200° C. to about 350° C. for about 3 hours to about 6 hours and optionally pressures of about 100 psi to about 2000 psi resulting in high temperature composites.

These polyimides have comparable properties to other high temperature polymers such as Dupont NR-150B2 as the data in Table I below on polymer and composite properties illustrates.

TABLE I

| Properties of Polymer | 3F | DuPont NR-150B2 |
|---|---|---|
| Glass transition temperature | 350° C. | 340° C. |

| Properties of Celion 6000/3F Composite | | |
|---|---|---|
| | RT | |
| | Flexural Strength ksi | Flexural Modulus $10^6$ psi |
| Celion 6000/3F | 125 | 19.8 |
| DuPont HMS/NR-150B2 | 126 | 21.0 |

| | Shear Strength, ksi | | |
|---|---|---|---|
| | RT | 600° F.(316° C.) | 662° F.(350° C.) |
| Celion 6000/3F | 8.55 | 3.5 | 4.4 |
| DuPont HMS/NR-150B2 | 7.40 | 4.6 | 4.6(343° C.) |

In contrast with other high temperature polymers these polyimides have superior high temperature properties when processed at lower temperatures and pressures. Evidence of this is that the above composite properties were comparable to the DuPont HMS/NR-150B2 composite even though that system is processed at 427° C. (800° F.) 2500 psi in contrast to the 325° C. 1000 psi processing conditions of this disclosure's polyimides. These lower processing conditions save energy and alleviate degradation of fibers, etc.

In addition, some 3F-dialkyl esters may be useful for high temperature lubricants or detergents.

These precursor monomers make a significant advance in the field of high temperature polymers. Either as solid polymers, fibers, films or when incorporated into composites they provide the strength properties at high temperatures desired for aerospace applications. Their excellent properties (e.g. fracture toughness, tensile strength, strain-to-failure) at high temperatures when processed at low temperatures and pressures give them a distinct advantage in this field of art. This advantage and the fact that they are processed from readily available cheap starting materials resulting in high yielding reactions facilitates their use in aerospace applications.

It should be understood that the invention is not limited to the particular embodiment shown and described herein, but that various changes and modifications may be made without departing from the spirit or scope of this concept as defined by the following claims.

I claim:

1. A fluorinated aromatic carboxylic acid monomer precursor for high temperature fluorinated polyimides comprising:

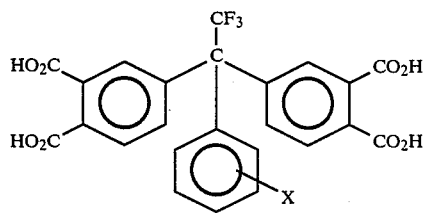

wherein X is hydrogen, carboxyl, sulfonic acid, hydroxy, low alkyl, halogen or nitro and hydrates of said acids.

2. The monomer as recited in claim 1 wherein x is hydrogen.

3. A fluorinated aromatic dianhydride monomer precursor for high temperature fluorinated polyimides comprising:

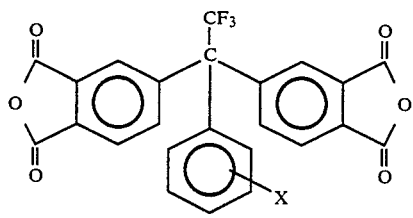

wherein x is hydrogen, carboxyl, sulfonic acid, hydroxy, low alkyl, halogen or nitro.

4. The monomer as recited in claim 3 wherein x is hydrogen.

5. A fluorinated aromatic dialkyl ester monomer precursor for high temperature fluorinated polyimides comprising:

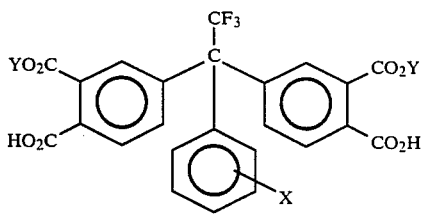

wherein X is hydrogen, carboxyl, sulfonic acid, hydroxy, low alkyl, halogen or nitro and Y is an alkyl group and hydrates of said esters.

6. The monomer as recited in claim 5 wherein X is hydrogen.

7. The monomer as recited in claim 5 wherein Y is methyl, ethyl, propyl or isopropyl.

8. The monomer as recited in claim 1 wherein X is hydrogen, carboxyl, sulfonic acid, hydroxy, methyl, halogen or nitro.

9. The monomer as recited in claim 3 wherein X is hydrogen carboxyl, sulfonic acid, hydroxy, methyl, halogen or nitro.

10. The monomer as recited in claim 5 wherein X is hydrogen, carboxyl, sulfonic acid, hydroxy, methyl, halogen or nitro.

* * * * *

UNITED STATES PATENT AND TRADEMARK OFFICE
CERTIFICATE OF CORRECTION

PATENT NO. : 4,863,640
DATED : September 5, 1989
INVENTOR(S) : Daniel A. Scola

It is certified that error appears in the above-identified patent and that said Letters Patent is hereby corrected as shown below:

Col. 2, line 63, replace "derivative" with --described--.

Col. 6, line 54, replace "3.28" with --3.38--.

Col. 6, line 68, replace "polymeric" with --polyamic--.

Col. 7, line 12, replace "structur" with --structure--.

Col. 7, line 30, replace "an" with --and--.

Col. 9, line 51, replace "polyimide" with --polyamide--.

Signed and Sealed this

Seventeenth Day of July, 1990

*Attest:*

HARRY F. MANBECK, JR.

*Attesting Officer*     *Commissioner of Patents and Trademarks*